United States Patent
Nerney

(12)
(10) Patent No.: US 6,368,308 B1
(45) Date of Patent: Apr. 9, 2002

(54) SYRINGE HAVING FORWARD-MOUNTED PLUNGER CONTROL

(76) Inventor: Michael E. Nerney, 10939 91st Ter. N., Seminole, FL (US) 33772

(*) Notice: Subject to any disclaimer, the term of this patent is extended or adjusted under 35 U.S.C. 154(b) by 0 days.

(21) Appl. No.: 09/398,570

(22) Filed: Sep. 17, 1999

(51) Int. Cl.⁷ ............................................... A61M 5/315
(52) U.S. Cl. ........................ 604/227; 604/218; 604/208
(58) Field of Search .................................. 604/207, 208, 604/218, 220, 111, 116, 117, 181, 187, 224, 227, 228, 229; 600/573, 576, 578

(56) References Cited

U.S. PATENT DOCUMENTS

| | | | |
|---|---|---|---|
| 2,295,849 A | | 9/1942 | Kayden |
| 2,735,427 A | | 2/1956 | Sullivan |
| 3,749,284 A | * | 7/1973 | Kloehn ........................ 604/208 |
| 3,819,091 A | | 6/1974 | Hollender |
| 4,109,653 A | | 8/1978 | Kozam et al. |
| 4,263,911 A | * | 4/1981 | McCormack et al. ........ 604/227 |
| 4,465,478 A | | 8/1984 | Sabelman et al. |
| 4,563,178 A | * | 1/1986 | Santeramo ................... 604/208 |
| 4,594,073 A | | 6/1986 | Stine |
| 4,639,248 A | * | 1/1987 | Schweblin ................... 604/227 |
| 4,664,128 A | | 5/1987 | Lee |
| 4,687,472 A | | 8/1987 | Gross |
| 4,711,250 A | | 12/1987 | Gilbaugh, Jr. et al. |
| 5,115,816 A | * | 5/1992 | Lee ............................ 604/187 |
| 5,159,933 A | * | 11/1992 | Hut |
| 5,163,907 A | | 11/1992 | Szuszkiewicz |
| 5,582,595 A | | 12/1996 | Haber et al. |
| 5,651,372 A | | 7/1997 | Caillouette |

* cited by examiner

*Primary Examiner*—Ronald Stright
(74) *Attorney, Agent, or Firm*—Ronald E. Smith; Smith & Hopen, P.A.

(57) ABSTRACT

A syringe has a slide member slideably mounted on the barrel of the syringe, and the slide member is interconnected to a plunger that is slideably mounted in the barrel so that movement of the slide member effects simultaneous and corresponding movement of the plunger. This allows a syringe operator to perform aspiration and injection in sequence with one-handed operation of the syringe. The slide member is mounted near the leading end of the barrel in trailing relation to the leading end of the plunger so that the operator can see the leading end of the plunger and control its instantaneous position by sliding the slide member with a thumb or finger. The hand position of the syringe operator does not change, assuring that precise needle positioning can be made and maintained even during procedures such as sclerotherapy where needle positioning is critical.

9 Claims, 3 Drawing Sheets

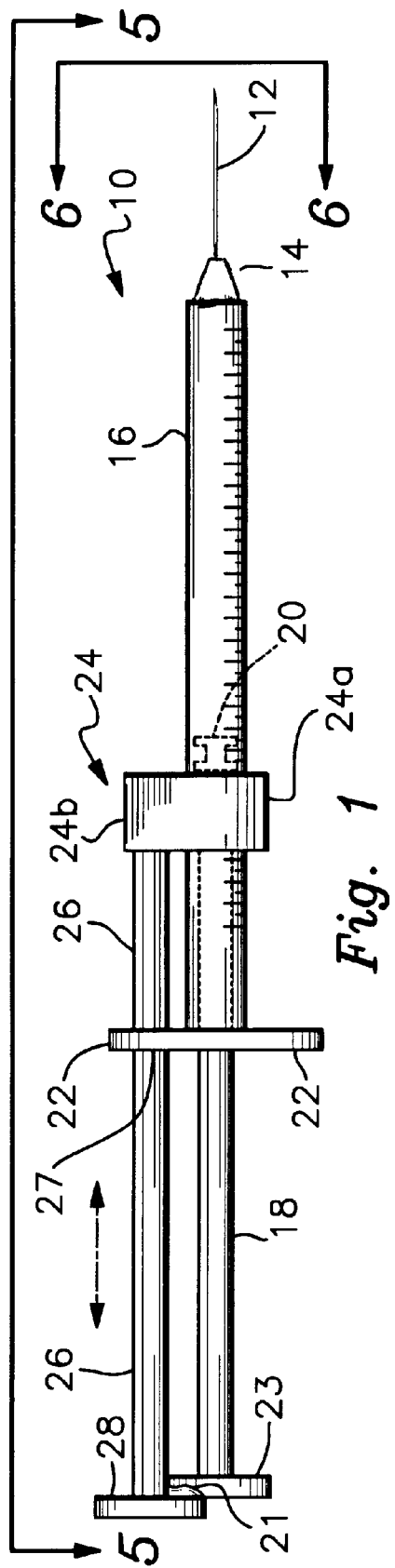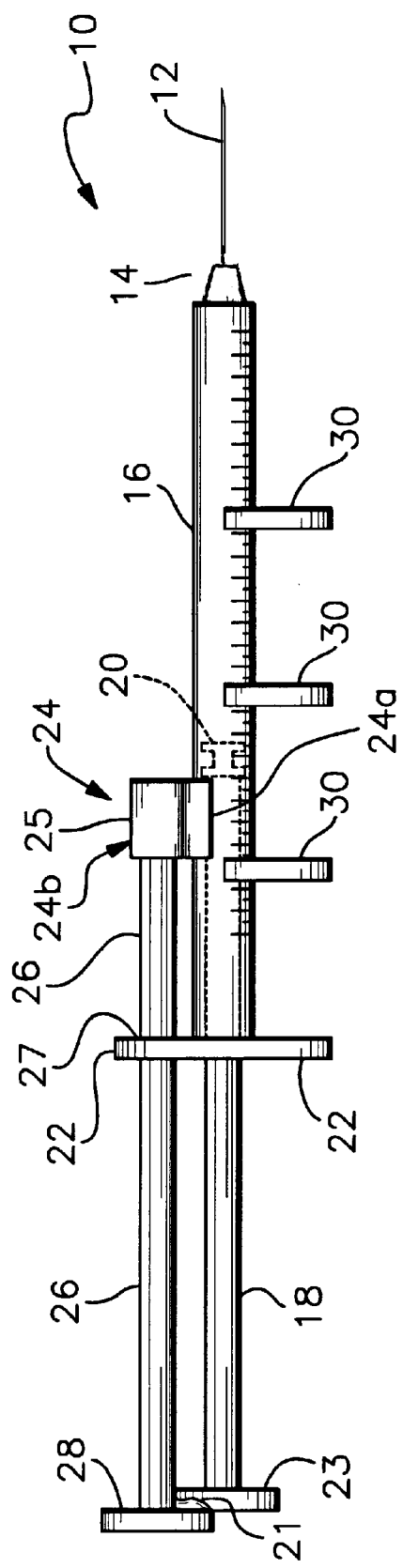

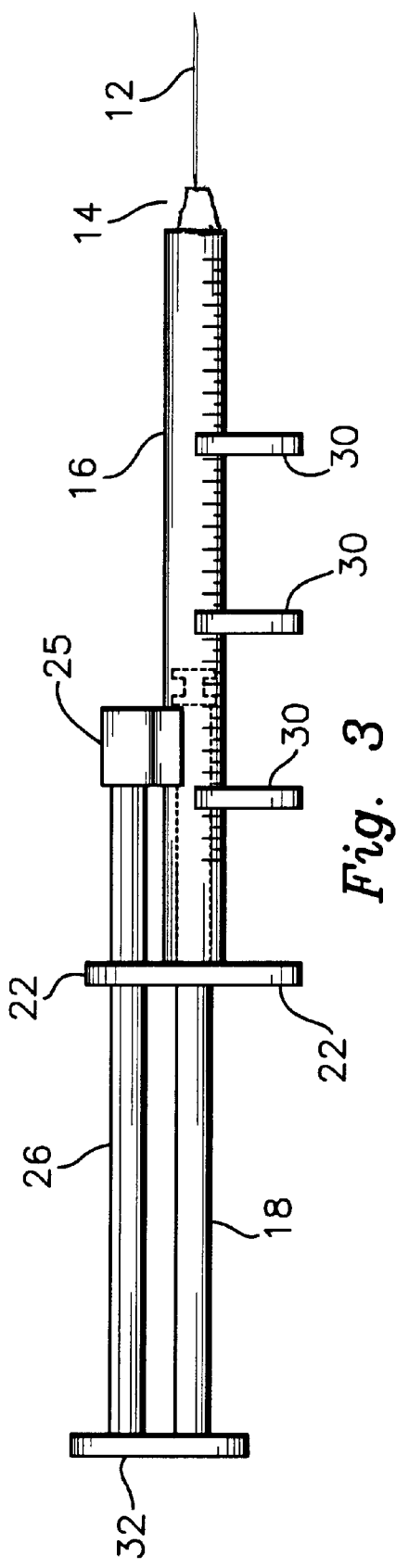
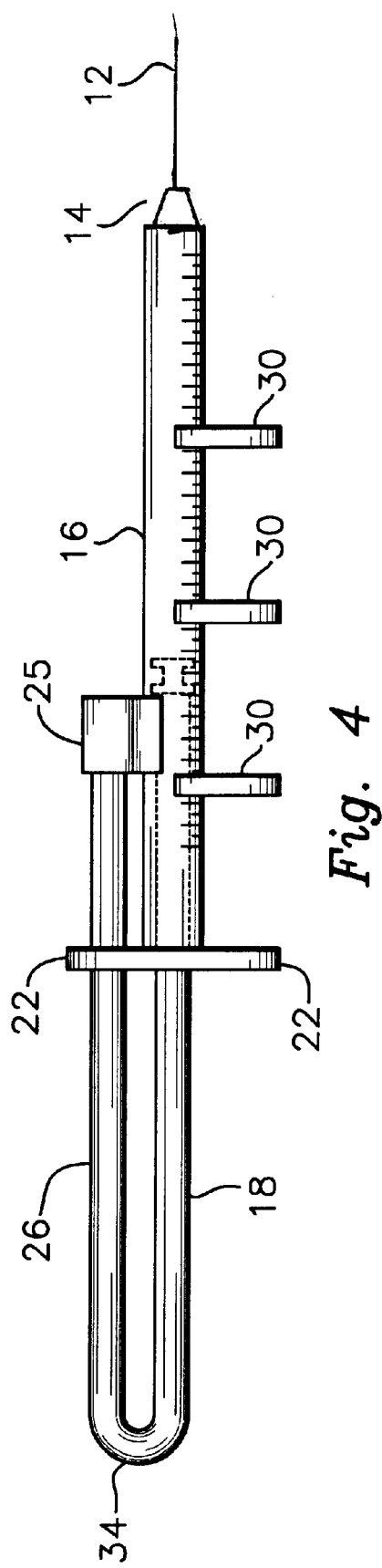

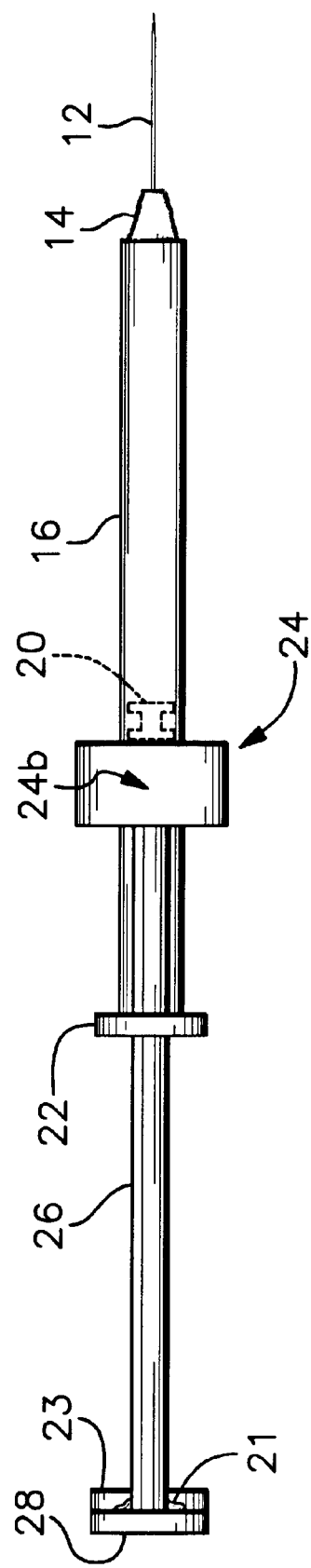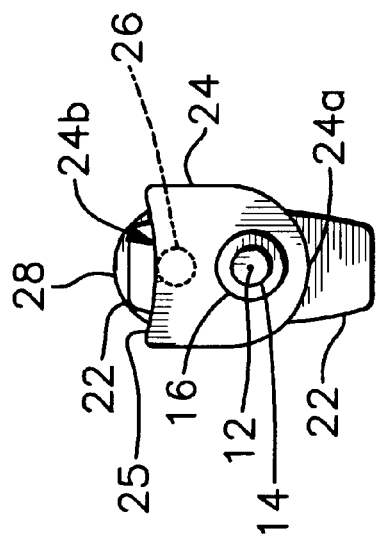
Fig. 5
Fig. 6

SYRINGE HAVING FORWARD-MOUNTED PLUNGER CONTROL

BACKGROUND OF THE INVENTION

1. Field of the Invention

This invention relates, generally, to syringes. More particularly, it relates to a syringe where the position of the plunger is controlled from a point near the leading end of the syringe.

2. Description of the Prior Art

A conventional syringe structure includes a needle held at its base by a hub that is mounted at the leading end of a barrel. A plunger is slideably mounted in the barrel, and a piston having annular seals is provided at the leading end of the plunger. In a syringe intended to be used as an aspirator, withdrawal of the piston/plunger in a leading-to-trailing direction creates a vacuum in the leading end of the barrel that pulls liquid fluid into the barrel. In a syringe intended to be used for injection, displacement of the piston/plunger in a trailing-to-leading direction drives a liquid fluid out of the barrel and through the needle into the patient's tissue.

Some syringes are used for aspiration and injection. Thus, the plunger is retracted to accomplish aspiration, and thereafter advanced to accomplish injection. When a conventional syringe is used in this manner, the physician must develop a technique whereby the needle remains properly positioned during the retraction and the advancement of the plunger. The most common way of performing an aspiration is for the operator to hold the barrel in a first hand and to retract the piston/plunger with a second hand. For injection, the operator usually employs a one-handed technique. The operator steadies the barrel by holding two laterally-extending tabs at the trailing end of the barrel with the index and middle fingers and by using the thumb to advance the plunger in a distal-to-proximal (trailing-to-leading) direction in a well-known way.

There are occasions, however, when it is necessary to inject substances in a precise location, such as a vascular space. Any inadvertent injection of the substance outside its intended target may harm the patient. For example, in the practice of sclerotherapy, a caustic substance is injected into superficial, diseased veins to destroy them. The veins may be quite small and thin-walled and they are typically difficult to calculate precisely with a needle tip. The patient experiences tissue destruction, ulceration and the pain concomitant therewith if the caustic substance is injected into tissue adjacent the diseased vein, so precision injection is a necessity. Accordingly, when performing an intravascular injection, the physician confirms needle tip location in the vascular space by aspiration until blood is seen. This requires retraction of the plunger. Injection, which requires advancement of the plunger, may then proceed.

The syringes now in use require the physician to change hand positions between the aspiration and the injection. Most physicians have developed their own personal techniques for controlling the plunger position with the same hand that holds the barrel of the syringe. These techniques include positioning a little finger on the trailing end of the plunger, holding the barrel in the palm of a hand so that the palm controls the plunger position, and other non-ergonomic techniques. The drawback of these techniques is that they require a high level of skill and cannot be repeated with consistency. Moreover, a change in hand position can lead to an accidental extravascular injection.

A number of syringes suitable for one-handed operation have been patented, but many of them are relatively complex in construction, difficult to use, and expensive to manufacture.

What is needed, then, is a syringe of the type that facilitates one-handed control during aspiration and injection. The improved syringe should reduce the level of skill required for its use. Moreover, it should have a simple construction, be easy to use, and should be economical to manufacture.

More particularly, a syringe is needed that enables sequential aspiration and injection with one hand in the absence of any need to change hand positions or to otherwise place the fingers, thumb or palm in an awkward position. The ideal syringe would enable the operator to control the instantaneous position of the plunger with a single digit such as a thumb or a finger without requiring movement of any other part of the hand. This would provide more stability so that accurate injection into the proper space could be accomplished. The control point should be positioned forwardly, near the needle, to facilitate its use.

However, it was not obvious to those of ordinary skill in this art how the needed syringe could be provided, in view of the art considered as a whole at the time the present invention was made.

SUMMARY OF THE INVENTION

The long-standing but heretofore unfulfilled need for an innovation that overcomes the limitations of the prior art is now met by a new, useful, and nonobvious invention. The novel syringe of this invention is adapted to be held in a single hand. The operator of the syringe can perform aspiration and injection in sequence without changing hand position. The syringe construction includes a needle, a hub for holding the needle, a barrel having a leading end to which the hub is mounted, an elongate plunger having a leading end slideably mounted within the barrel and a trailing end that is external to the barrel, and a slide member that slideably engages an external surface of the barrel. A yoking means interconnects the slide member to the trailing end of the plunger. The slide member is adapted to be controlled by a thumb or finger of a user so that manipulation of the slide member controls an instantaneous position of the plunger.

The slide member is positioned at a leading end of the barrel, in closely spaced trailing relation to the leading end of the plunger so that the syringe operator can easily observe the respective positions of the slide member and the forward end of the plunger at the same time.

The slide member includes a first part for slideably engaging the barrel and a second part adapted for abutting engagement by a thumb or finger. The first part conforms to a curvature of the barrel and the second part is relatively flat to provide an ergonomic support surface for a thumb or finger.

The first part may encircle the barrel, having an inner diameter slightly greater than an outer diameter of said barrel.

Alternatively, the first part may be arcuate in configuration and extend more than one hundred eighty degrees in circumference around the barrel so that the barrel is slideably captured therewithin.

The yoking means includes an elongate rod disposed in substantially parallel relation to the plunger and interconnecting means for connecting the elongate rod to the plunger. The elongate rod has a leading end secured to the slide member and a trailing end connected to the trailing end of the plunger.

A guide means is mounted to a trailing end of the barrel for maintaining the elongate rod in substantially parallel relation to the plunger. The guide means is provided in the form of an apertured or slotted tab mounted at the trailing end of the barrel; the aperture or slot slideably receives the elongate rod.

The interconnecting means includes a first transversely disposed flange secured to the trailing end of the elongate rod and a second transversely disposed flange secured to the trailing end of the plunger. The flanges have a diameter sufficient to cause them to abut one another, and an adhesive means is provided to secure the flanges to one another.

The interconnecting means alternatively includes a flat plate adhesively secured to respective trailing ends of the elongate rod and plunger.

In another embodiment, the interconnecting means includes a return bend that interconnects respective trailing ends of the elongate rod and plunger.

A plurality of longitudinally spaced apart, radial projections may also be mounted along the extent of the barrel to provide finger-receiving spaces therebetween. These projections keep the fingers and hand from moving relative to the syringe during operation of the syringe.

It is a primary object of this invention to provide a syringe for performing one-handed aspiration and injection in sequence in the absence of any need to reposition the hand at any time.

Another object is to provide a syringe structure having means mounted externally of the syringe barrel for controlling an instantaneous position of the plunger.

These and other important objects, features, and advantages of the invention will become apparent as this description proceeds.

The invention accordingly comprises the features of construction, combination of elements and arrangement of parts that will be exemplified in the construction hereinafter set forth, and the scope of the invention will be indicated in the claims.

BRIEF DESCRIPTION OF THE DRAWINGS

For a fuller understanding of the nature and objects of the invention, reference should be made to the following detailed description, taken in connection with the accompanying drawings, in which:

FIG. 1 is a side elevational view of a first embodiment of the invention;

FIG. 2 is a side elevational view of a second embodiment thereof;

FIG. 3 is a side elevational view of a third embodiment thereof;

FIG. 4 is a side elevational view of a third embodiment thereof;

FIG. 5 is a top plan view of the first embodiment; and

FIG. 6 is a front end view of the first embodiment.

DETAILED DESCRIPTION OF THE PREFERRED EMBODIMENT

Referring now to FIG. 1, it will there be seen that an exemplary embodiment of the invention is denoted as a whole by the reference numeral 10.

Syringe 10 includes needle 12, tapered hub 14, barrel 16, and plunger 18. Hub 14 is secured to the leading end of barrel 16 and holds the base of needle 12 in a well-known way. The leading end of plunger 18 is sealed as at 20 so that liquid drawn into barrel 16 during aspiration does not leak therepast. The seal also prevents medication from leaking therepast when the syringe is used for injection.

A pair of laterally-extending tabs, collectively denoted 22, are provided at the trailing end of barrel 16, and flange 23 is provided at the distal end of plunger 18.

Slide member 24 has a first part 24a that slideably engages the external surface of barrel 16, and may completely surround barrel 16 as depicted in FIGS. 1 and 6. Alternatively, as depicted in FIGS. 2–4, slide member first part 24a may have an arcuate construction that extends slightly more than one hundred eighty degrees about the circumference of barrel 16 to capture the barrel therewithin. If slide member first part 24a extends less than one hundred eighty degrees about said circumference, elongate grooves, not shown, are formed in barrel 16 and transversely disposed opposite ends of slide member first part 24a are adapted to slidingly fit within said grooves.

Slide member 24 has a second part 24b that surmounts first part 24a and which may be integrally formed therewith. Its top surface 25 is preferably ergonomically designed to comfortably support a thumb or finger, as perhaps best disclosed in connection with the end view of FIG. 6.

Elongate rod 26 has a leading end mounted to second part 24b of slide member 24. Flange 22 is apertured or slotted as at 27 to slideably receive elongate rod 26. Flange 28 is formed at the trailing end of said elongate rod.

Flanges 23 and 28 overlap as depicted in FIGS. 1 and 2; accordingly, a suitable adhesive 21 may be employed to secure said flanges to one another and thereby interconnect plunger 18 and elongate rod 26 to one another.

As depicted in FIG. 2, a plurality of longitudinally spaced apart projections, collectively denoted 30, may be provided in those embodiments where slide member 24 does not include a barrel-encircling first part 24a. Each projection 30 is disposed in radial relation to a longitudinal axis of barrel 16. The fingers of the syringe operator are placed between said projections to further ensure against hand movement during aspiration and injection. It is also worth noting that the part of flange 22 that depends from the trailing end of barrel 16 in parallel, longitudinally-aligned relation to projections 30 may be positioned between the third ("ring") and fourth ("little") fingers, or between the second ("middle") and third fingers, or even between the first and second fingers when the syringe is used. A thumb is placed atop top surface 25 of slide member 24, the just-mentioned part of flange 22 is positioned between preselected fingers, and the thumb is used to displace slide member 24 as desired. When the syringe is handled in this manner, there is no need for projections 30. The syringe is held naturally when in use, resting atop the fingers, with the user's thumb resting atop the top surface of the slide member in opposing relation to the fingers.

As depicted in FIG. 3, plunger 18 and elongate rod 26 could be made without flanges 23 and 28 as their respective trailing ends. In that case, flat connecting plate 32 is adhered to said respective trailing ends.

Moreover, as depicted in FIG. 4, plunger 18 and elongate rod 26 may be interconnected by return bend 34.

Still further means for interconnecting plunger 18 and elongate rod 26 are within the scope of this invention because numerous interconnection means will be obvious to those of ordinary skill in the art of machine design, in view of this disclosure.

The interconnection of plunger 18 and elongate rod 26 provide conjoint movement between said parts. More particularly, it ensures simultaneous and corresponding movement of thumb-supporting surface 25 and the leading end of plunger 18. Thumb-supporting surface 25 is slightly distal of the leading end of said plunger to enable the physician to look directly at the needle and to manipulate slide member 24 as needed while doing so. No special skill is required to slide said slide member rearwardly, i.e., in a proximal-to-distal or leading-to-trailing direction when aspirating blood into barrel 16, or forwardly, i.e., in a distal-to-proximal or trailing-to-leading direction when performing an injection. The forward and rearward sliding motion is a very simple motion that does not require the physician to re-grip the barrel or to otherwise re-position his or her hand during a procedure. Thus, the physician can pay maximum attention to proper needle location, and need not develop the skill of manipulating the trailing end of a plunger with a little finger or a palm.

This invention represents a major breakthrough in the art of syringes. Being drawn to a pioneering invention, the claims that follow are entitled, as a matter of law, to broad interpretation to protect the heart or essence of the invention from piracy.

It will thus be seen that the objects set forth above, and those made apparent from the foregoing description, are efficiently attained. Since certain changes may be made ill the foregoing construction without departing from the scope of the invention, it is intended that all matters contained in the foregoing construction or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

Now that the invention has been described.

What is claimed is:

1. A syringe, comprising:
   a needle;
   a hub for holding said needle;
   a barrel having a leading end to which said hub is mounted;
   an elongate plunger having a leading end slideably mounted within said barrel and a trailing end that is external to said barrel;
   a slide member that slideably engages an external surface of said barrel; and
   yoking means for interconnecting said slide member to said trailing end of said plunger;
   said slide member adapted to be controlled by a digit of a user so that manipulation of said slide member controls an instantaneous position of said plunger;
   said slide member being positioned at a leading end of said barrel;
   said yoking means including an elongate rod disposed in substantially parallel relation to said plunger and interconnecting means for connecting said elongate rod to said plunger, said elongate rod having a leading end secured to said slide member and a trailing end connected to said trailing end of said plunger;
   said interconnecting means including a first transversely disposed flange secured to the trailing end of said elongate rod, a second transversely disposed flange secured to the trailing end of said plunger, said first and second transversely disposed flanges having a diameter sufficient to cause them to abut one another, and adhesive means for securing said flanges to one another;
   whereby said syringe is adapted to be held in a single preselected hand; and
   whereby no change in hand position is needed between a retraction of said plunger in a leading-to-trailing direction relative to said barrel and advancement of said plunger in a trailing-to-leading direction relative to said barrel.

2. The syringe of claim 1, whereby said slide member includes a first part for slideably engaging said barrel and a second part adapted for abutting engagement by a thumb or finger.

3. The syringe of claim 2, wherein said first part conforms to a curvature of said barrel and said second part is relatively flat to provide a support surface for supporting said digit.

4. The syringe of claim 3, wherein said first part encircles said barrel and has an inner diameter slightly greater than an outer diameter of said barrel.

5. The syringe of claim 1, further comprising a guide means mounted to a trailing end of said barrel for maintaining said elongate rod in substantially parallel relation to said plunger.

6. The syringe of claim 5, wherein said guide means is provided in the form of an apertured tab mounted at the trailing end of said barrel, said aperture slideably receiving said elongate rod.

7. The syringe of claim 1, wherein said interconnecting means includes a flat plate adhesively secured to respective trailing ends of said elongate rod and said plunger.

8. A syringe, comprising:
   a needle;
   a hub for holding said needle;
   a barrel having a leading end to which said hub is mounted;
   an elongate plunger having a leading end slideably mounted within said barrel and a trailing end that is external to said barrel;
   a slide member that slideably engages an external surface of said barrel; and
   yoking means for interconnecting said slide member to said trailing end of said plunger;
   said slide member adapted to be controlled by a digit of a user so that manipulation of said slide member controls an instantaneous position of said plunger;
   said slide member being positioned at a leading end of said barrel;
   said yoking means including an elongate rod disposed in substantially parallel relation to said plunger and interconnecting means for connecting said elongate rod to said plunger, said elongate rod having a leading end secured to said slide member and a trailing end connected to said trailing end of said plunger;
   said interconnecting means including a return bend that interconnects respective trailing ends of said elongate rod and said plunger;
   whereby said syringe is adapted to be held in a single preselected hand; and
   whereby no change in hand position is needed between a retraction of said plunger in a leading-to-trailing direction relative to said barrel and advancement of said plunger in a trailing-to-leading direction relative to said barrel.

9. A syringe, comprising:

a needle;

a hub for holding said needle;

a barrel having a leading end to which said hub is mounted;

said barrel having an upper exterior surface and a lower exterior surface;

a flange disposed at a trailing end of said barrel;

said flange having an upper part that projects upwardly relative to said upper exterior surface of said barrel;

said flange having a lower part that projects downwardly from said lower exterior surface of said barrel;

an elongate plunger having a leading end slideably mounted within said barrel and a trailing end that is external to said barrel;

a slide member having a bottom part that slideably engages said upper external surface of said barrel;

said slide member having an upper part adapted for abutting engagement by a thumb;

said lower part of said flange adapted to be positioned between preselected fingers of a user when said user's thumb is positioned in abutting relation to said upper part of said slide member;

yoking means for interconnecting said slide member to said trailing end of said plunger;

said yoking means including an elongate rod disposed in substantially parallel relation to said plunger;

said elongate rod having a leading end secured to said slide member and a trailing end connected to said trailing end of said plunger.

said slide member adapted to be controlled by said thumb so that manipulation of said slide member controls an instantaneous position of said plunger;

said slide member being positioned at a leading end of said elongate rod;

said lower exterior surface of said barrel disposed in supported, overlying relation to a user's fingers and said upper part of said slide member disposed in underlying relation to said user's thumb when said syringe is in use;

whereby said syringe is adapted to be held and supported in a single preselected hand;

whereby said syringe is adapted to rest atop and be supported by said user's fingers;

whereby an instantaneous position of said barrel is controlled by movement of said user's thumb; and whereby said preselected fingers and said user's thumb oppose one another when the syringe is used.

* * * * *